(12) United States Patent
Savich et al.

(10) Patent No.: US 7,425,595 B2
(45) Date of Patent: *Sep. 16, 2008

(54) SUPERABSORBENT POLYMER PRODUCTS INCLUDING A BENEFICIAL ADDITIVE AND METHODS OF MAKING AND APPLICATION

(75) Inventors: Milan H. Savich, Beaverton, OR (US); Gary S. Olson, Salem, OR (US); Eddie W. Clark, Salem, OR (US); William McKee Doane, Morton, IL (US); Steven William Doane, Scottsburg, IN (US)

(73) Assignee: Absorbent Technologies, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/500,698

(22) Filed: Aug. 8, 2006

(65) Prior Publication Data

US 2007/0015878 A1    Jan. 18, 2007

(51) Int. Cl.
   C08H 5/04 (2006.01)
   C08B 37/00 (2006.01)
   C09D 103/04 (2006.01)

(52) U.S. Cl. ............... 525/242; 428/327; 428/402; 428/403; 525/54.3; 525/330.1; 525/360; 527/103; 527/312

(58) Field of Classification Search .......... None
   See application file for complete search history.

(56) References Cited

U.S. PATENT DOCUMENTS

| | | | |
|---|---|---|---|
| 3,244,500 A | 4/1966 | Stinson | 71/1 |
| 3,935,099 A | 1/1976 | Weaver et al. | 210/43 |
| 3,981,100 A | 9/1976 | Weaver et al. | 47/58 |
| 3,985,616 A | 10/1976 | Weaver et al. | 195/63 |
| 3,997,484 A | 12/1976 | Weaver et al. | 260/17.4 GC |
| 4,076,663 A * | 2/1978 | Masuda et al. | 525/54.31 |
| 4,093,542 A | 6/1978 | Dahmen et al. | 210/54 |
| 4,113,685 A | 9/1978 | Hubner et al. | 260/29.4 |
| 4,134,863 A | 1/1979 | Fanta et al. | 260/17.4 GC |
| 4,155,888 A | 5/1979 | Mooth | 527/314 |
| 4,194,998 A | 3/1980 | Fanta et al. | 260/17.4 GC |
| 4,323,487 A | 4/1982 | Jones et al. | 525/54.32 |
| 4,408,073 A | 10/1983 | Hubner et al. | 523/130 |
| 4,459,068 A | 7/1984 | Erickson | 405/264 |
| 4,483,950 A | 11/1984 | Fanta et al. | 524/48 |
| 4,528,350 A | 7/1985 | Goossens et al. | 526/307 |
| 4,711,919 A | 12/1987 | Peppmoller et al. | 524/77 |
| 4,766,173 A | 8/1988 | Bailey et al. | 524/819 |
| 4,773,967 A | 9/1988 | Peppmoller et al. | 162/168.2 |
| 4,983,390 A | 1/1991 | Levy | 424/404 |
| 5,118,719 A | 6/1992 | Lind | 521/92 |
| 5,122,544 A | 6/1992 | Bailey et al. | 521/40.5 |
| 5,147,343 A | 9/1992 | Kellenberger | 604/368 |
| 5,154,713 A | 10/1992 | Lind | 604/358 |
| 5,176,797 A | 1/1993 | Hartan et al. | 162/168.3 |
| 5,221,313 A | 6/1993 | Mortvedt et al. | 71/63 |
| 5,292,404 A | 3/1994 | Hartan et al. | 162/164.6 |
| 5,350,799 A * | 9/1994 | Woodrum et al. | 525/54.3 |
| 5,512,646 A | 4/1996 | Hartan et al. | 526/292.95 |
| 5,567,478 A | 10/1996 | Houben et al. | 427/342 |
| 5,821,286 A | 10/1998 | Xu et al. | 524/47 |
| 5,853,848 A | 12/1998 | Fisk | 428/143 |
| 5,856,370 A | 1/1999 | Chmelir | 521/128 |
| 5,965,149 A | 10/1999 | Silver | 424/405 |
| 6,048,467 A | 4/2000 | Dahmen et al. | 252/8.57 |
| 6,221,832 B1 | 4/2001 | Casteel et al. | 510/446 |
| 6,228,964 B1 | 5/2001 | Hartan et al. | 526/307 |
| 6,232,285 B1 | 5/2001 | Casteel et al. | 510/446 |
| 6,303,560 B1 | 10/2001 | Hartan et al. | 510/446 |
| 6,660,819 B2 | 12/2003 | Chmelir et al. | 526/217 |
| 6,758,152 B2 | 7/2004 | Steadman | 111/128 |
| 6,800,712 B2 | 10/2004 | Doane et al. | 52/312 |
| 6,889,471 B2 | 5/2005 | Arnold et al. | 47/58.1 SC |
| 7,009,020 B2 * | 3/2006 | Doane et al. | 527/103 |
| 2003/0020043 A1 * | 1/2003 | Barresi et al. | 252/194 |
| 2004/0074271 A1 | 4/2004 | Krysiak et al. | 71/27 |
| 2006/0047068 A1 * | 3/2006 | Doane et al. | 525/54.3 |
| 2006/0058502 A1 * | 3/2006 | Doane et al. | 530/200 |
| 2007/0015878 A1 * | 1/2007 | Savich et al. | 525/242 |
| 2007/0044528 A1 | 3/2007 | Kitchen | 71/28 |

OTHER PUBLICATIONS

Burkhardt et al."Plastic,Processing", Ullmann's Encyclopedia of Industrial Chemistry, Abstrct and pp. 1-5, Jun. 15, 2000.*

Stockosorb Agro; David W. Cox, 2004 Scholarship Report available at: http://nuffield.com.au/report_f/2004/David%20Cox%202004%20report.pdf (Aug. 19, 2006).

(Continued)

Primary Examiner—Vasu Jagannathan
Assistant Examiner—Gennadiy Mesh
(74) Attorney, Agent, or Firm—Stoel Rives LLP

(57) ABSTRACT

A superabsorbent polymer combined with a beneficial additive and method for administering the same in agricultural applications is disclosed. A method for delivering a beneficial additive in agricultural applications includes obtaining a beneficial additive combined with a superabsorbent starch graft copolymer and dispensing the combined beneficial additive and superabsorbent polymer in an agricultural environment.

31 Claims, No Drawings

OTHER PUBLICATIONS

Press release titled, "A New Way of Reducing Water Consumption". (Nov. 7, 2001) http://ewire.com/displayccfm/Wire_ID/809.

Mikkelsen, Robert L.; "Using Hydrophilic Polymers to Control Nutrient Release" Fertilizer Research 38: 53-59, 1994.

Mikkelsen, Robert L. et al.;"Addition of Gel-Forming Hydrophilic Polymers to Nitrogen Fertilizer Solutions". Fertilizer Solutions, Fertilizer Research 36: 55-61, 1993.

Thompson, C. A.; "Effects of Stockosorb on Grain Sorghum in Central Kansas". 1998 Kansas Fertilizer Research Report of Progress 829; p. 36-46; Kansas State University-Manhattan, Kansas.

Thompson, C. A.; "Effects of the Cross-Linked Polyacrylamide Stockosorb on Wheat, Triticale, and Grain and Forage Sorghums in Central Kansas". 1999 Kansas Fertilizer Research Report of Progress 847; p. 21-35; Kansas State University-Manhattan, Kansas.

Thompson, C. A.; "Effects of the Cross-Linked Polyacrylamide Stockosorb on Winter Wheat, Triticale, and Grain and forage Sorghum in Central Kansas". 2000 Kansas Fertilizer Research Report of Progress 868; p. 29-40; Kansas State University-Manhattan, Kansas.

Office Action mailed on Mar. 19, 2007 in regard to U.S. Appl. No. 11/013,664.

Office Action mailed on Aug. 8, 2007 in regard to U.S. Appl. No. 11/013,664.

Office Action mailed on Jan. 16, 2007 in regard to U.S. Appl. No. 11/269,214.

Office Action mailed on Sep. 17, 2007 in regard to U.S. Appl. No. 11/269,214.

Office Action mailed on Oct. 22, 2007 in regard to U.S. Appl. No. 11/213,563.

Office Action mailed on May 9, 2007 in regard to U.S. Appl. No. 11/213,563.

"Starch-Encapsulated Pesticides: ARS Papers Presented at the International Seminar on Research and Development of Controlled-Release Formulations of Pesticides". Vienna, Austria Sep. 6-10, 1993 United States Department of Agriculture; Agricultural Service; 1995-1; Nov. 1994.

* cited by examiner

SUPERABSORBENT POLYMER PRODUCTS INCLUDING A BENEFICIAL ADDITIVE AND METHODS OF MAKING AND APPLICATION

RELATED APPLICATIONS

This application claims the benefit of U.S. patent application Ser. No. 11/013,664, filed Dec. 15, 2004 and entitled METHODS OF MAKING AND USING A SUPERABSORBENT POLYMER PRODUCT INCLUDING A BIOACTIVE, GROWTH-PROMOTING ADDITIVE, which claims the benefit of U.S. Provisional Application Ser. No. 60/529,949, filed Dec. 15, 2003, which are both incorporated herein by reference.

The claimed invention was made as a result of activities undertaken within the scope of a joint research agreement between Milan H. Savich, Steven Doane and William Doane.

TECHNICAL FIELD

The present disclosure relates to superabsorbent polymer products and to methods for making and delivering superabsorbent polymer products including beneficial additives.

DETAILED DESCRIPTION

Superabsorbent polymers ("SAPs") are materials that imbibe or absorb at least 10 times their own weight in aqueous fluid and that retain the imbibed or absorbed aqueous fluid under moderate pressure. The imbibed or absorbed aqueous fluid is taken into the molecular structure of the SAP rather than being contained in pores from which the fluid could be eliminated by squeezing. Some SAPs can absorb up to, or more than, 1,000 times their weight in aqueous fluid.

SAPs may be used in agricultural or horticultural applications. The terms "agricultural" and "horticultural" are used synonymously and interchangeably throughout the present disclosure. The term "agricultural environment" refers to plants, roots, seedlings, seeds, or the plant growing media, such as soil, in proximity to plants, roots, seedlings, or seeds. Applying SAPs to soil or other plant-growing media in agricultural settings have resulted in earlier seed germination and/or blooming, decreased irrigation requirements, increased propagation, increased crop growth and production, decreased soil crusting, increased yield and decreased time of emergence.

Synthetic SAPs are commercially available and are conventionally used in conjunction with baby or adult diapers, catamenials, hospital bed pads, cable coating and the like. However synthetic SAPs may also be used in agricultural applications.

Additionally, starch graft copolymers are another type of SAP product that may be used in agricultural applications. Starch graft copolymers typically comprise a monomer graft polymerized onto a polysaccharide, such as a starch or cellulose. Starch graft copolymers are typically used to absorb aqueous fluids for use in absorbent softgoods, in increasing the water holding capacity of soils, and as coatings onto seeds, fibers, clays, and the like.

In one embodiment, a superabsorbent polymer product includes a starch graft copolymer and a beneficial additive entrapped within the starch matrix of the starch graft copolymer. The terms "entrapped" and "encapsulated" as used herein are meant to refer to the fact that the beneficial additive is physically held by the starch matrix portion of the SAP product.

The term "beneficial additive" is meant to include any additive that promotes plant, root, seedling, or seed growth, either directly or indirectly. Indications of promotion of growth include, but are not limited to, increased crop yield, growth rate, seed germination, and/or plant size, earlier seed germination and/or blooming, decreased irrigation requirements, increased propagation, increased crop growth, increased crop production, decreased soil crusting, increased root development, decreased depredation, stronger/heartier plants, and plants less susceptible to disease. For example, this may be accomplished indirectly through the use of additives that are used to control weeds, diseases, and repel or kill insects, nematodes, or other crop pests and combinations thereof.

In some situations, beneficial additives are conventionally applied in an agricultural environment at low doses, such that the active ingredient of the beneficial additive is mixed with a suitable carrier to facilitate distribution over the area to be treated. In some cases certain additives may be relatively insoluble in water. These water-insoluble additives may then be combined with alternative solvents or diluents and surfactants to create an additive formulation. The additive formulation may improve the ease of handling the additive. A particular additive may have several formulations that achieve different objectives. Some objectives may include, increased toxicity to the target, decreased toxicity to the applicator, increased persistence in the agricultural environment, greater retention, reduced drift, reduced volatility, or greater penetration of foliage. Exemplary additive formulations may include, but are not limited to, emulsions, solutions of water or oil, wettable powders, flowables where solid particles are suspended in a liquid or semi-liquid, granulars and dusts.

The SAP product containing a beneficial additive may be applied or dispensed in an agricultural environment, such as to a growing substrate in proximity to a plant, root, seed, or seedling, or directly to a plant, root, seed, or seedling. The starch-based SAP product including a beneficial additive promotes growth of a plant, root, seed, or seedling placed in proximity to the SAP product by promoting the availability of beneficial nutrients to the plant, root, seed, or seedling.

The absorptivity of the starch matrix of the starch-based SAP product facilitates entrapment of the beneficial additive in the starch matrix, thereby minimizing disassociation or release of the beneficial additive from the starch matrix due to heavy rainfall, squeezing, or jarring of the SAP product during transport or manufacture, and during application of the SAP product. Because the beneficial additive is entrapped in the SAP product, the runoff rate of the additive may be significantly less than the runoff rate of additives that are applied directly to soil, plants, roots, seedlings, or seeds without the SAP. Consequently, the retention time of the beneficial additive is extended compared to conventional application of the beneficial additive. The additive is maintained in the SAP matrix and diffuses to the plant, root or seedling over time.

Without begin bound by theory, it is believed that plants, roots, and seedlings withdraw the active portion of the beneficial additive from the starch-based SAP product through capillary action, and that seeds utilize the beneficial additive by diffusion of the additive from the starch matrix.

An exemplary method of forming a SAP product including a beneficial additive for use in agricultural applications involves (1) graft polymerizing at least one type of monomer onto a starch to form a starch graft copolymer including a starch matrix; (2) isolating the resulting starch graft copolymer; (3) forming particles of starch graft copolymer that are sized for use in agricultural applications; and (4) adding the beneficial additive so that at least some of the beneficial additive is entrapped by the starch matrix. The step of adding the beneficial additive may occur at various times during this process, depending on the type of additive and the desired degree of entrapment of the additive within the starch matrix.

One embodiment of a method of producing a starch graft copolymer SAP including a beneficial additive for use in agricultural applications involves graft polymerizing acrylonitrile onto a starch in the presence of an initiator, such as a ceric (+4) salt, to form the starch graft copolymer, and saponifying the nitrile groups with an alkali metal, such as potassium hydroxide or sodium hydroxide to convert nitrile groups into a saponificate having alkali carboxylate and carboxamide groups. Addition of the beneficial additive may optionally occur while combining the monomer and the starch. Alternatively, addition of the beneficial additive may occur following saponification of the mixture. The starch graft copolymer may then be precipitated.

In one embodiment, precipitation occurs via an acid titration. Acid, such as hydrochloric acid, nitric acid, sulfuric acid, or phosphoric acid may be added until a pH of between about 2.0 and about 3.5, more particularly about 3.0, is reached. The resulting precipitate may be washed with water to remove the salts, and if necessary, separated in some manner. Separating methods include settling, centrifuging, and other mechanical means of separating.

The carboxylic acid of the starch graft copolymer may then be titrated back to the alkali form with the hydroxide of an alkali metal, such as potassium hydroxide, to a pH of between about 4.0 and about 9.0, more particularly about 7.0. The desired pH level may depend on the beneficial agent used since some insecticides and fungicides are pH sensitive.

The resulting viscous mass may then be forced through a die plate, dusted to remove tackiness, and air or oven dried. The dried particles are then screened to the appropriate size. If desired, the particles could be ground to fine particles then formed into pellets of the desired size for use in agriculture. The beneficial additive may be introduced after precipitation of the viscous mass, or alternatively, after forming the starch graft copolymer particles.

In another embodiment, the isolated product is recovered from the viscous saponificate with the use of water miscible solvents such as alcohols. These include, for example, methanol, ethanol, propanol and isopropanol. The resulting dough may be immersed into the alcohol, and the alkali starch graft copolymer is precipitated into particles that are optionally screened after drying to the desired size. Alternatively, the starch graft copolymer may be isolated through the use of an extruder, such as through a heated screw. The beneficial additive may optionally be introduced after forming the starch graft copolymer particles.

Another embodiment of a method of producing a starch graft copolymer SAP including a beneficial additive for use in agricultural applications involves (1) graft polymerizing a monomer, other than acrylonitrile, onto a starch in the presence of an initiator to form a starch graft copolymer; (2) cross-linking the starch graft copolymer, for example, by adding a cross-linking agent; (3) adjusting the pH of the cross-linked starch graft copolymer, e.g., neutralization; (4) isolating the cross-linked starch graft copolymer; and (5) drying the cross-linked starch graft copolymer. Addition of the beneficial additive may occur at various times during this process. Exemplary times to add the beneficial additive are (1) while graft polymerizing the monomer onto the starch; (2) following pH adjustment; and (3) following formation of the particles of starch-based SAP product.

Exemplary monomers for use in this embodiment of forming a SAP product include acrylic acid or methacrylic acid. Exemplary monomers may also include acrylamide or methacrylamide. Sulfonic acids, such as 2-acrylamido-2-methylpropanesulfonic acid (AMPS) and vinyl sulfonic acid may also be used. Moreover, acrylates, such as ethyl acrylate and potassium acrylate may also be used. Derivatives and mixtures of the above-listed monomers may also be desirable.

In applications using acrylic acid, the addition of acrylamide thereto may help induce graft polymerization and adds to absorbency of the SAP. By way of example, the ratio by weight of acrylic acid to acrylamide may be about 2:1. Alternatively, the ratio of acrylic acid to acrylamide may also range up to a ratio of 9:1 and beyond. Because acrylamide is considered a neurotoxin, it may be desirable to reduce the relative amount of acrylamide to acrylic acid, while using enough to help induce graft polymerization of acrylic acid.

Exemplary initiators for graft polymerizing a monomer onto a starch include cerium (+4) salts, such as ceric ammonium nitrate; ammonium persulfate; sodium persulfate; potassium persulfate; ferrous peroxide; ferrous ammonium sulfate-hydrogen peroxide; L-ascorbic acid; and potassium permanganate-ascorbic acid. Other suitable initiators known to those skilled in the art may be used, such as alternative persulfates and peroxides, as well as vanadium, manganese, etc. The amount of initiator used may vary based on the chosen initiator, the selected monomer, and the chosen starch. Some initiators, e.g., persulfates, may require the presence of heat. The initiator may be added in a single or multiple steps, and multiple initiators may be used.

In alternative applications, acrylic acid may graft polymerize onto a starch or other polysaccharide without the assistance of acrylamide. For example, acrylic acid may polymerize when placed under heat and/or pressure. Polymerization without the addition of acrylamide may be accomplished, for example, in a heated screw extruder, such as a single screw or a double screw.

According to one embodiment, the starch graft copolymer may then be cross-linked, for example, by adding a chemical cross-linking agent to form a cross-linked starch graft copolymer. It may be desirable for the starch graft copolymer to be cross-linked if it dissolves in aqueous fluids previous to being cross-linked. Cross-linking is one method to permit the starch graft copolymer to absorb aqueous fluids without dissolving. However, the amount of cross-linking agent added is typically indirectly proportional to the absorbency of the resulting SAP product.

Exemplary cross-linking agents include: glycerides; diepoxides; diglycidyls; cyclohexadiamide; methylene bis-acrylamide; bis-hydroxyalkylamides, such as bis-hydroxypropyl adipamide; formaldehydes, such as urea-formaldehyde and melamine-formaldehyde resins; isocyanates including di- or tri-isocyanates; epoxy resins, typically in the presence of a base catalyst; and derivatives and mixtures thereof.

Alternative methods of cross-linking may also be employed. For example, a solid SAP product may be cross-linked through irradiation, such as through gamma or x-rays or an electron beam. Irradiation facilitates cross-linking of the starch graft copolymer by creating free radicals in the copolymer chain. In some applications, after irradiation an annealing or melting process may be used to re-form the cross-linked copolymer chains. Furthermore, it may be desirable to perform at least one step of the cross-linking by irradiation process in an atmosphere relatively free of oxygen.

Although the addition of cross-linking agents may be desirable in the production of SAPs, self-cross-linking copolymers may also be used. In a self-cross-linking copolymer, either a single self-reactive functional group or multiple self-reactive functional groups or multiple co-reactive functional groups are incorporated into the mixture. One exemplary co-reactive functional group is a copolymer of acrylic acid and glycidyl methacrylate.

The pH of the cross-linked starch graft copolymer may be adjusted to a desired value for the particular agricultural application. For example, the cross-linked starch graft copolymer may be neutralized to convert the carboxyl groups to potassium salts. Alternative pH values may be desirable depending upon the type of soil and the type of crop the resulting SAPs will be applied to. The resulting pH for most agricultural applications typically will range from about 4.0 to about 9.0. The desired pH may be greater or less than this range depending on the requirements for the particular agricultural application.

Alternatively, in some embodiments, pH adjustment of the starch graft copolymer may occur prior to cross-linking. Exemplary solvents that may be used to effect pH adjustment include potassium hydroxide, potassium methoxide, or a mixture thereof, any of which may optionally be diluted in methanol or other solvents.

In alternative embodiments, pH adjustment may not be necessary. For instance, if potassium acrylate were used as the monomer in lieu of acrylic acid, the resulting product may already be within an acceptable pH range.

The resulting pH-adjusted, cross-linked starch graft copolymer may then be isolated. As discussed previously, the beneficial additive may have already been introduced into the starch graft copolymer dough. However, the beneficial additive may also be introduced after the SAP is isolated. One exemplary method of isolation involves simply drying the cross-linked starch graft copolymer, such as, for example, on a heated drum or via air-drying. The dried SAP product may then be pelletized according to pelletization methods known to those having skill in the art. According to this embodiment, isolation of the SAP product may be achieved in an alcohol-free environment.

In another embodiment, the step of isolating the starch graft copolymer involves extruding the cross-linked starch graft copolymer such as through a heated screw to form granules of SAP product. To minimize re-agglomeration of the granules, the granules may be coated with a dusting agent that decreases their propensity to stick together. Exemplary dusting agents include cellulose, clay, starch, flour, and other natural or synthetic polymers that prevent the granules from sticking together. Alternatively, the granules may be lightly sprayed with methanol to prevent them from sticking together, and/or the extrusion can be performed under high pressure.

Yet another exemplary method of isolating the starch graft copolymer involves precipitating the pH-adjusted, cross-linked starch graft copolymer using water-miscible solvents such as alcohols, e.g., methanol, ethanol, propanol, and isopropanol. Immersing the cross-linked starch graft copolymer in alcohol may cause the alkali starch graft copolymer to precipitate into particles that are later screened to the desired size after drying. The alcohol removes the water and extraneous salts from the cross-linked starch graft copolymer.

Another exemplary implementation of this method of precipitation involves blending sufficient methanol into the pH-adjusted, cross-linked starch graft copolymer to achieve a smooth dispersion. The smooth dispersion may then be pumped into a precipitation tank, which may include a stirring system that can vigorously mix the methanol while pumping in the smooth cross-linked starch graft copolymer dispersion. Once mixed, the resulting methanol and cross-linked starch graft copolymer particles may be collected by decanting or washing with methanol or centrifuged and collected, then dried to a moisture level of between about 1 percent and about 20 percent.

Another implementation of the isolation step through precipitation with methanol involves wetting the surface of the cross-linked starch graft copolymer with a small amount of methanol and then chopping the cross-linked starch graft copolymer into larger "chunks" that will not re-adhere to one another. Once the surface of the starch graft copolymer has been wetted with methanol, the resulting material is slippery to the touch and is no longer sticky. This effect may be achieved by using a compositional ratio of between about one part and about two parts of methanol per one part of solid.

Once the methanol has been added, the cross-linked starch graft copolymer may be pumped through an in-line chopper to form chunks having a diameter of less than one inch or, alternatively, hand-chopped with scissors. In one embodiment, the resulting mixture is then fed into a tank or Waring blender that has between about 1.5 gallons and about 4.0 gallons of additional methanol per pound of cross-linked starch graft copolymer. In some embodiments, the cross-linked starch graft copolymer may be subject to a pulverizer, in the presence of methanol, such as an in-line mixer or disintegrator which breaks the mass into smaller pieces as desired for the particular application. The methanol in the larger tank may be agitated with a Cowles dissolver or other mixer capable of achieving high speeds.

Yet another implementation of the isolation step through precipitation with methanol involves pre-forming the particle size before the methanol precipitation step. The use of dies to form strands or rods having different shapes and diameters can improve the particle size formation process. This particular implementation offers enhanced control of the final particle size. The cross-linked starch graft copolymer (neutralized or unneutralized) may be forced through a die plate having holes of varying diameter (e.g., about $1/16$ inch to more than $1/4$ inch) and varying shapes (e.g., round, star, ribbon, etc.).

Methods of forcing the cross-linked starch graft copolymer through the die plate include using a hand-operated plunger, screw feeding, auguring, pumping, and any other commonly known method. The resulting strands or rods may be placed into the precipitation tank without any further addition of methanol as a premixing agent. The strands or rods may be treated to prevent them from sticking together by, for example, wetting or spraying the strands or rods with methanol or dusting them with a dusting agent, such as, for example, cellulose, clay, starch, flour, or other natural or synthetic polymers. The resulting strands or rods may be precipitated with agitated methanol, removed from the tank, and dried.

Depending on the agricultural application, the final SAP product may be granular and have a particle size that is courser than about 300 mesh. For example, in some applications where the starch graft copolymer is applied directly into the soil with the crop, the particle size is courser than about 50 mesh, such as between about 8 to about 25 mesh. This particle size range correlates to commercially available granule applicators. Therefore, alternative particle sizes may be used. To broadcast or meter the starch-based SAP particles through existing agricultural application equipment, an 8 mesh to about 25 mesh granular, starch-based SAP product having a density of between about 25 lbs per cubic foot and about 35 lbs per cubic foot, such as 32 lbs per cubic foot.

Finer particle sizes are typically used in seed coating or root dipping applications. By way of example, the particle size for seed coating may be between about 75 and about 300 mesh, such as about 100 mesh. For root coating, the particle size may be between about 30 mesh and about 100 mesh, such as about 50 mesh.

Alternatively, the cross-linked starch graft copolymer product may be mixed with a solvent, such as water, to form a slurry or gel. For example, in applications where the SAP product is to be dispensed via a spray applicator, it may be desirable for the SAP product to be in substantially liquid form. In one such embodiment, the concentration, by weight, of the starch graft copolymer within the SAP product (combination of beneficial additive and starch graft copolymer) ranges from about 0.5 percent to about 2.0 percent, such as about 1.0 percent. Having the starch graft copolymer in this concentration allows the SAP product to be flowable, but also retains the absorbent properties of the SAP to be effective in releasing the beneficial additive over time.

In the methods and compositions described for manufacturing starch graft copolymers, the beneficial additive may be added to the SAP dough or particles such that it is substantially distributed throughout. One exemplary method by which addition of the beneficial additive may occur involves dissolving the additive in a solvent and then spraying the solution of beneficial additive onto the SAP dough or onto the particles of SAP product (with or without agitation of the dough or particles during addition).

A second exemplary method of adding the beneficial additive involves forming a slurry of additive and adding the slurry to the SAP dough or particles at any point during processing. One reason for adding the beneficial additive following formation of the particles of SAP product is that the highly absorptive nature of the particles results in their readily imbibing the additive. In one embodiment, the particles of starch-based SAP product are dried following application of the beneficial additive.

The beneficial additives disclosed herein generally fall into one of two categories: water-soluble additives and water-insoluble additives. Water-soluble additives may be added directly to the SAP dough or particles at any point during processing or during application of the SAP product to the growing substrate. According to one method described above, the water-soluble additives may be added to the SAP dough following saponification or following formation of the particles of SAP product. This is because the timing of the addition of the beneficial additive during combination of the grafting reagent(s) and the starch may result in the additive being washed out during the saponification step.

Water-insoluble beneficial additives may be added at various points during processing, to the SAP particles, or during application of the SAP product to the growing substrate. Typically, water-insoluble additives are dissolved in a solvent, e.g., a water-miscible solvent such as alcohol, and then the solution is applied to the SAP dough, SAP particles, or to the growing substrate. Following application of the solution or slurry of the dissolved beneficial additive, the solvent may be removed from the SAP dough or particles by heating or drying to drive off residual solvent by evaporation.

Exemplary beneficial additives include fertilizers, pesticides, bioactive materials, plant-growth hormones, plant-growth regulators, plant activators, kelp products, and soil-based nutrients and derivatives thereof. A list of exemplary pesticides includes acaricides, algicides, antifeedants, avicides, bactericides, bird repellents, chemosterilants, fungicides, herbicide safeners, herbicides, insect attractants, insect repellents, insecticides, mammal repellents, mating disruptors, molluscicides, nematicides, rodenticides, synergists, and virucides. Exemplary microbial pesticides include bacillus thuringiensis and mycorrhizal fungi. Exemplary insecticides include, but are not limited to, thiodan, diazinon, and malathion. In some embodiments more than one beneficial additive may be included in the SAP product.

Exemplary commercially available pesticides include, but are not limited to: Admire™ (imidacloprid) manufactured by Bayer, Regent™ (fipronil) manufactured by BASF, Dursban™ (chlorpyrifos) manufactured by Dow, Cruiser™ (thiamethoxam) manufactured by Syngenta, Karate™ (lambda-cyhalothrin) manufactured by Syngenta, and Decis™ (deltamethrin) manufactured by Bayer. A combination or blend of pesticides may also be used. Alternative pesticides may also be used as would be apparent to those having skill in the art.

Exemplary commercially available fungicides include, but are not limited to: Amistar™ (azoxystrobin) manufactured by Syngenta, Folicur™ (tebuconazole) manufactured by Bayer, Opus™ (epoxiconazole) manufactured by BASF, Dithane™ (mancozeb) manufactured by Dow, Flint™ (trifloxystrobin) manufactured by Bayer, and Ridomil™ (metalaxyl) manufactured by Syngenta. Fungicides may help control or prevent the growth of mold or fungus on the roots, seeds or seedlings thus inhibiting root or seed rot. A combination or blend of fungicides may also be used. Alternative fungicides may also be used as would be apparent to those having skill in the art.

By way of example, fungicides, such as methyl bromide, may be conventionally applied to the soil surface and covered with a plastic material to prevent loss. Incorporating the fungicide with the SAP product may help to entrap the fungicide on and in the soil or other plant growing media. Occasional, periodic irrigation may keep the SAP product moist and help prevent the UV degradation of the SAP product.

Exemplary commercially available herbicides that may be used as a beneficial additive include, but are not limited to: Roundup™ (glyphosate) manufactured by Monsanto, Gramoxone™ (paraquat) manufactured by Syngenta, Harness™ (acetochlor) manufactured by Monsanto, Prowl™ (pendimethalin) manufactured by BASF, Dual™ (metolachlor) manufactured by Syngenta, and Puma™ (fenoxaprop) manufactured by Bayer. Furthermore, a combination or blend of herbicides may be used. Alternative herbicides may also be used as would be apparent to those having skill in the art.

Exemplary commercially available plant-growth regulators that may be used as a beneficial additive include, but are not limited to: Ethrel™ (ethephon) manufactured by Bayer, Pix™ (mepiquat) manufactured by BASF, Dropp™ (thidiazuron) manufactured by Bayer, Finish™ (cyclanilide) manufactured by Bayer, and Royal MH™ (maleic hydrazide) manufactured by Crompton. A combination or blend of growth regulators may be used. Furthermore, growth inhibitors, growth retardants, growth stimulants, and derivatives and mixtures thereof may be included. Alternative growth regulators or hormones may also be used as would be apparent to those having skill in the art. Moreover, combinations of different beneficial agents may be used, such as pesticides and fungicides and plant hormones, etc.

Exemplary soil-based nutrients that may optionally be used as the beneficial additive include calcium, magnesium, potassium, phosphorus, boron, zinc, manganese, copper, iron and other metals, sulfur, nitrogen, molybdenum, silicon, ammonium phosphate, fish meal, organic compounds and additives, organic based fertilizers derived from plant and animal products, and derivatives, blends, and mixtures thereof. More information about exemplary growth-promoting additives can be found in *The Farm Chemicals Handbook* published by Meister Publishing Company.

Exemplary polysaccharides that may be used in the starch graft copolymer of the SAP product include cellulose, starches, flours, and meals. Exemplary starches include native starches (e.g., corn starch (Pure Food Powder, manufactured by A.E. Staley), waxy maize starch (Waxy 7350, manufactured by A.E. Staley), wheat starch (Midsol 50, manufactured by Midwest Grain Products), potato starch (Avebe, manufactured by A.E. Staley)), dextrin starches (e.g., Stadex 9, manufactured by A.E. Staley), dextran starches (e.g., Grade 2P, manufactured by Pharmachem Corp.), corn meal, peeled yucca root, unpeeled yucca root, oat flour, banana flour, and tapioca flour. The starch may be gelatinized. An exemplary starch is gelatinized cornstarch. Furthermore, according to one embodiment, the weight ratio of the starch to the monomer is in the range of between about 1:1 and about 1:6.

Fillers, absorbents, carriers, and surfactants which may affect the processability or efficacy of the beneficial additive may be used to form the starch-based SAP product. Exemplary carriers include Kaolin clay, Fullers Earth, diatomaceous earth products, ungelatinized granular starch, silicates, blends thereof, mixtures thereof, and derivatives thereof. Typically, the swellability of the starch-based SAP product decreases with increased proportions of clay. The processing point at which the fillers, absorbents, carrier, and surfactants are added may vary depending upon the desired characteristics of the resulting SAP product. Two exemplary points of addition of a filler, absorbent, carrier, or surfactant are (1) preblending with the starch and (2) separate addition during downstream processing.

The release rate of the starch-based SAP product may be affected by its particle size. For example, pelletized particles may release the active portion of the beneficial additive more gradually than granular products of equal surface area. Additionally, the release rate may be dependent upon whether the beneficial agent is incorporated into the matrix of the starch graft copolymer or whether it is coated on the outside of the SAP particle.

Application of the SAP product to a plant, root, seed, or seedling may occur by various methods, including, but not limited to (i) dipping the plant, root, seed, or seedling into SAP product particles, a slurry of SAP product particles, or a paste including the SAP product particles; (ii) mixing dirt, soil, fertilizer, or another plant growth media with the SAP product particles and later planting a plant, root, seed, or seedling into the plant growth media/SAP product mixture; and (iii) forming a slurry of SAP product that is applied directly to the growing substrate.

One exemplary method of applying the starch-based SAP product with a beneficial additive includes using a spray applicator to spray the foliage of a plant or to spray a seed, seedling or plant growing media. Alternatively, a flowable SAP may be sprayed onto a beneficial additive, such as fertilizer to reduce the breakdown and movement of dry fertilizers in the soil.

Conventionally, beneficial additives, such as a pesticide, applied to the foliage of a plant, are subject to several variables. These variables include, among others, the beneficial additive may volatize from the leaf surface and be lost to the atmosphere, the beneficial additive may wash from the leaf surface due to rainfall, the beneficial additive may remain on the leaf surface and dry to a crystalline form or viscous liquid, the beneficial additive may penetrate the plant cuticle and go no further, and the beneficial additive may move completely through the cuticle. The use of the SAP product in foliar applications may help control these variables.

The amount of foliar coverage may depend on the type and amount of additive movement. For example, the additive may be systemic and translocate from roots to leaves and vice versa. Additionally, some beneficial additives, such as phenoxies, are mobile in soil and may be translocated in plants, while other additives are effective only on contact. The use of SAP products may help provide more accurate and effective application to the primary target site of action. The primary target site of action is the specific location on a plant, root, seed, seedling or growing media to which a given beneficial additive is primarily effective.

In spray applications the SAP product may be in substantially liquid form, or some form of slurry. In one such embodiment, the concentration, by weight, of the starch graft copolymer within the SAP product (combination of beneficial additive and starch graft copolymer) ranges from about 0.5 percent to about 2.0 percent, such as about 1.0 percent. Having the starch graft copolymer in this concentration allows the SAP product to be flowable, but also retains the absorbent properties of the SAP to be effective in releasing the beneficial additive over time. However, the addition of the beneficial agent may reduce the absorbency of the SAP product, and a higher concentration of SAP may be needed, such as up to about four percent.

In spray applications, the starch graft copolymer portion of the SAP product may act as a tackifier to keep the beneficial additive adhered to the primary target site of action. For instance, if the beneficial additive is most effective when applied to the leaf of a plant, the starch graft copolymer gives the SAP product a tackiness that helps it adhere to and remain on the leaf of the plant when applied. Consequently, the beneficial additive is effectively applied and maintained on the primary target site of action. Conventionally, if the beneficial additive was applied without the SAP, the additive may fall from the primary target site of action to the ground resulting in a less effective application.

In spray applications, the amount of beneficial additive applied per unit area may be a function of the swath treated, the flow rate from the spray applicator, the forward speed of the applicator and the viscosity of the SAP product. By way of example, one embodiment of the SAP product may be applied by using a flat fan nozzle, cone nozzle or other type of liquid application equipment.

In spray applications, the SAP product may be prepared in slurry form. The slurry may have a viscosity that allows the slurry to be sprayed through a spray nozzle, such as a standard farm spray nozzle. In one embodiment, the SAP product having a mesh size of between about 16 mesh to about 30 mesh may be used to prepare the slurry containing the beneficial agent. In alternative embodiments, a mesh size from about 30 mesh to about 100 mesh may also be used.

In one exemplary embodiment, tebuconazole, such as the product sold under the brand Folicur® by Bayer CropScience, may be used as the beneficial agent in the SAP product. Conventionally, about 4 to about 8 fluid ounces of tebuconazole is applied per acre, diluted with 20 gallons or greater of water per acre using ground sprayers or about 10 gallons or greater of water per acre using aircraft. To increase the efficacy of the beneficial agent a small amount of SAP product may be added, such as about one pound per acre. However, to provide the superabsorbent benefits of the SAP product, a larger amount of SAP product may be used per acre, such as between about seven and about eight pounds. It should be noted that with the larger amount of SAP product, additional water may be needed to form a slurry that is sprayable through a standard farm spray nozzle.

In another embodiment, iprodione, such as the product sold under the brand Rovral® by Bayer CropScience, may be used as the beneficial agent in the SAP product. Conventionally, iprodione is applied at approximately 1 to about 2 pints per acre. However, iprodione may be applied at different concentrations depending upon the crop. A typical maximum concentration is from about 1 to about 2 pints for every about 40 to about 50 gallons of water per acre. A typical minimum concentration is from about 1 to about 2 pints for every about 100 to about 200 gallons of water per acre. As with tebuconazole, the amount of iprodione may be prorated to the SAP concentration level to get the proper coverage of SAP product with beneficial agent per acre.

In yet another embodiment of the spray application of the starch-based SAP product with a beneficial additive involves using metalaxyl as the beneficial agent, such as the product sold under the brand Ridomil® by Syngenta. Metalaxyl is typically applied at about 0.5 to about 2 pints per acre with sufficient water to provide uniform coverage and incorporate the beneficial agent in the top two inches of soil. For example, this may include between about 20 gallons of water to about 150 gallons of water per acre. As with tebuconazole and iprodione, the amount of water that is used to combine the SAP product and metalaxyl may be prorated. For example, a dilution ration of about 15 parts water to one part metalaxyl may be used.

Alternatively, the SAP product may be in the form of a hydrogel for use with root dipping and similar applications. The viscosity of the hydrogel may be greater than that of the slurry used in spray applications.

Another exemplary method of applying the starch-based SAP product with a beneficial additive involves applying the granular starch-based SAP product onto the plant growing media in proximity to a plant, seed, seedling or root. For example, the granule SAP product may be applied using a granule applicator such as manufactured under the trademarks John Deere, Gandy or Microband. Alternatively, the granule SAP product may be incorporated into a cellulose mat and the like. In yet other embodiments, the SAP product may be applied with the use of a cultivator. A dry pesticide applicator, fumigator, injector and aerial sprayer may alternatively be used.

Furthermore, the SAP product may be applied by shanking into the ground as a layby application. In such a method, the SAP product containing a beneficial additive is deposited in the growing media adjacent the root system of a growing plant or deposited adjacent the anticipated location of a plant root system before planting or germination of a seed. In the layby application, as with the other methods of application disclosed herein, the SAP product including the beneficial additive may be in granular form where the beneficial additive is entrapped within the starch matrix or coated around the granular SAP particle or a combination of both. Additionally, an injector may be used to deliver the SAP product including the beneficial additive.

According to another exemplary method of applying a SAP product containing a beneficial agent is in seed coating. In seed coating applications, the SAP particle size may be finer than those used in granular applications. The beneficial agent may be disposed on the surface of the SAP particle, within the matrix of the SAP particle, or both. The seed coating SAP product may optionally include the combination of a binding agent and the SAP product with a solvent, such as water, to form a slurry that is applied to the seed. Alternatively, the dry SAP product may be combined with a binder or tackifier, such as, for example, a mineral, gypsum, or clay, to form a mixture that will stick to the seed. These methods can also be used to prepare a coating to be applied to any of a plant, root, seed, or seedling.

The SAP product containing a beneficial additive may also be prepared as a slurry or hydrogel for use as a root dip. For example, in one embodiment of a root dip application, between about 3 oz. and about 6 oz. of SAP product with about 5 gallons of water is combined to form a slurry that may be applied to the growing substrate and/or to the plant, root, seed, or seedling.

One potential benefit offered by the starch-based SAP product including a beneficial additive is that it may increase the effectiveness of carrying nutrients, etc. to seedling, roots, seeds, and plants. For example, pesticides attacking generalized biochemical target sites can be rendered more species selective, i.e., targeting specific weeds or pests, by structural optimization. A pesticide, or alternative beneficial agent, which is conventionally used in a general application may be more species selective because of the effectiveness in target applications. In this process, the target site interaction of the pesticide nucleus may be preserved, but the structure of the compound may be modified to improve specificity.

Further, starch controlled-release matrices may provide a reduction in leaching, groundwater contamination, toxicity, odor, volatility, and decompositional problems, such as photodecomposition, compared to conventional application of beneficial additives not entrapped in a starch matrix. For example, volatilization represents one mode of loss of beneficial additives, such as pesticides, from points of ground or structure application. These losses may take place by vapor loss from plant or soil surfaces after application and incorporation as well as via evaporation of fine spray particles that do not reach the primary target site during application. For instance, 2,4-D is a herbicide that is volatile above a certain temperature. Without being bound by theory, it is believed that the SAP matrix reduces the cleavage of ester groups in the herbicide, thereby reducing volatility.

Additionally, beneficial additives that are temperature sensitive may be preserved over a longer period of time when used in conjunction with a SAP particle versus conventional applications of the beneficial additive. For example, the starch graft copolymer product may act as an anti-transpiration agent. The amount of water lost by a plant during transpiration may depend on the plant size along with the surrounding light intensity, temperature, humidity, wind speed and water supply. The application of the SAP product may decrease the transpiration rate and thereby preserve and protect plants from drying out too quickly. Furthermore, the application of the SAP product containing a beneficial additive may prevent the plant from evaporating water quickly in elevated temperatures when applied as a foliar application. In one application, the SAP product containing a beneficial additive may be coated on fruit, which may prevent the fruit from drying out as fast and provide a protective layer against pests, funguses, diseases and the like.

The combination of starch graft copolymers and beneficial additives also may provide for various release mechanisms. For instance, a delayed release, a slow release, a quick release and a pulsating release of additive from the SAP product can be achieved depending upon the SAP particle and the formulation of the beneficial additive.

According to one exemplary release mechanism, a beneficial additive applied to the surface of the SAP product may be released into the surrounding environment before the beneficial additive that is incorporated into the matrix of the SAP product is released. Furthermore, the release mechanism and rate of the beneficial agent may also be proportional to the particle size of the SAP product. Another method of controlling the release mechanism may include layering multiple beneficial agents on the SAP product resulting in alternative release times dependent upon the particular layer in which the beneficial agent is located.

In another embodiment, a binder may also be incorporated into the SAP product. The binder may couple the beneficial additive to the SAP particle. The type of binder may help control the desired controlled release mechanism for release of the encapsulated beneficial additive after and/or over a desired period of time. For example, temperature sensitive binders may be used to release the beneficial additive upon achieving a particular temperature, etc.

The use of a starch graft copolymer with a beneficial additive may also include the benefit of biodegradability, in that the starch graft copolymer can break down into carbon dioxide, water and nitrogen within a measurable time. Furthermore, the abundant availability, low cost, and physical nature of starches (especially cornstarch) in the United States make the starch-based SAP product including a beneficial additive relatively inexpensive to manufacture.

Another potential benefit of incorporating beneficial additives with the starch graft copolymer includes a reduction in drift of the beneficial additive compared to conventional applications. The SAP particle may help keep the beneficial additive in a localized area because of its weight, providing for a more site-specific application to a target area with minimal drift. Minimizing drift also may provide an environmental benefit of reducing the runoff of the additive into aquifers or outside of the treated areas. Moreover, because of the increase in the efficiency of the beneficial additive when coupled with the starch graft copolymer, less additive may be needed per application to achieve the same results in conventional applications. Additionally, the use of the SAP product may help reduce residual phototoxicity.

It is recognized that entrapment efficiency, swellability, release rate, and efficacy of the starch-based SAP product can be affected to various degrees by the types of materials used, the processing conditions implemented, and the degree and type of ex-situ downstream processing. Because composition and processing conditions may be selected to maximize product performance and processing efficiency, desirable processing parameters, such as temperature, solids concentration, concentration of starch, concentration of beneficial additive, type of additive, number of additives, levels of addition, addition processes, and addition timing, vary greatly. For this reason, the following examples are intended only to further illustrate exemplary embodiments of the present disclosure.

EXAMPLE 1

Spray Application of Asset™ Pesticide to SAP Particles

Distilled water (1,400 ml) was placed in a 3-liter resin kettle and was subjected to constant agitation with a stirrer. Starch flour or meal (110 g) was slowly added to the kettle, and the resulting mixture was stirred for approximately five minutes. A slow stream of nitrogen gas was added to the mixture while the mixture was heated until it reached a temperature of approximately 95° C. Upon reaching this temperature, the mixture was maintained at this temperature and stirred for approximately 45 minutes to ensure that the starch was gelatinized. The heating mantle was then removed, and the resin kettle was placed in a cold-water bucket bath. The mixture was continuously stirred under nitrogen until the temperature reached 25° C. Acrylonitrile (115 g) and 2 acrylamido-2-methyl-propanesulfonic acid (23 g) were added. The resulting mixture was continuously stirred under nitrogen for approximately 10 minutes. A catalyst solution including cerium ammonium nitrate (5.5 g) dissolved in 0.1M nitric acid solution (50 ml) was added to the mixture while the mixture cooled. The mixture was continuously stirred under nitrogen while the resin kettle remained in the cold-water bucket for approximately 60 minutes. The temperature of the mixture at the end of the 60 minutes was approximately 40° C. A solution including potassium hydroxide flakes (90 g) dissolved in water (200 g) was added to the mixture during stirring and heating. The mixture was stirred and heated until a temperature of 95° C. was achieved, after which the mixture was stirred for an additional 60 minutes. The mixture was then neutralized to a pH of 7.5 using a 10% solution of hydrochloric acid. The resulting dough was then cooled to a temperature of about 40° C. The viscous dough was precipitated in methanol using one of the above-described precipitation methods to produce SAP particles.

The resulting SAP particles were subjected to a Fertilizer Analysis Test that analyzed the presence of various bioactive components. The results are reproduced in Table I to allow the reader to compare the SAP product with the starch-based SAP product of the present invention.

TABLE I

Fertilizer Analysis of an SAP Product Without an Additive.

| Nutrient | % Available |
|---|---|
| Nitrogen | 3.04 |
| Ammonia | <0.01 |
| Phosphorus | <0.10 |
| $P_2O_5$ | N/A |
| Potassium | 17.66 |
| $K_2O$ | 21.28 |
| Calcium | <0.01 |
| Magnesium | <0.01 |
| Sodium | 0.08 |
| Boron | <20.0 |
| Iron | 39.96 |
| Manganese | <10.0 |
| Copper | <10.0 |
| Zinc | <10.0 |
| Monoammonium Phosphate | N/A |

Trial A: Application of Asset™ Pesticide at a Concentration of 3 Pints/Acre

Using a standard, commercially available garden sprayer, approximately 3 pints of Asset™ was sprayed onto 10 lbs. of SAP product having a mesh size of between about 10 and about 20 and formed using the above-described method. The SAP particles were agitated during application of the Asset™ pesticide, to ensure that the beneficial additive thoroughly coated the SAP particles. Asset™ pesticide has a slight green tint, and thus the application of Asset™ pesticide to the SAP particles resulted in their being slightly tinted green. The resulting starch-based SAP particles were subjected to a Fertilizer Analysis Test that analyzed the presence of various bioactive components. The results are reproduced in Table II.

TABLE II

Fertilizer Analysis of the SAP Product Formed in Trial A.

| Nutrient | % Available |
|---|---|
| Nitrogen | 3.85 |
| Ammonia | 0.13 |
| Phosphorus | 2.61 |

TABLE II-continued

Fertilizer Analysis of the SAP Product Formed in Trial A.

| Nutrient | % Available |
|---|---|
| $P_2O_5$ | 5.97 |
| Potassium | 16.06 |
| $K_2O$ | 19.35 |
| Calcium | <0.01 |
| Magnesium | <0.01 |
| Sodium | 0.13 |
| Boron | 74.08 |
| Iron | 288.93 |
| Manganese | 165.65 |
| Copper | 151.97 |
| Zinc | 160.67 |
| Monoammonium Phosphate | 1.07 |

Trial B: Application of Asset™ Pesticide at a Concentration of 8 Pints/Acre

Using a standard, commercially available garden sprayer, approximately 8 pints of Asset™ pesticide was sprayed onto 10 lbs of SAP product having a mesh size of between about 10 and about 20 and formed using the above-described method. The SAP particles were agitated during application of the Asset™ pesticide, to ensure that the beneficial additive thoroughly coated the SAP particles. Asset™ pesticide has a slightly green tint, and thus the application of Asset™ pesticide to the SAP particles resulted in their being slightly tinted green. The resulting starch-based SAP particles were subjected to a Fertilizer Analysis Test that analyzed the presence of various bioactive components. The results are reproduced in Table III.

TABLE III

Fertilizer Analysis of the SAP Product Formed in Trial B.

| Nutrient | % Available |
|---|---|
| Nitrogen | 4.76 |
| Ammonia | 0.62 |
| Phosphorus | 5.90 |
| $P_2O_5$ | 13.51 |
| Potassium | 15.07 |
| $K_2O$ | 18.16 |
| Calcium | <0.01 |
| Magnesium | <0.01 |
| Sodium | 0.20 |
| Boron | 166.17 |
| Iron | 629.38 |
| Manganese | 373.84 |
| Copper | 340.36 |
| Zinc | 353.38 |
| Monoammonium Phosphate | 5.09 |

EXAMPLE 2

Slurry Application of Asset™ Pesticide to SAP Particles

SAP particles having a mesh size of between about 20 and about 40 were made according to the method described in Example 1. Approximately 25 g of SAP particles were combined with 1 L of an aqueous slurry of Asset™ pesticide. The resulting slightly green-tinted slurry was agitated to ensure that the Asset™ pesticide was evenly distributed throughout the slurry. The slurry was subjected to a Fertilizer Analysis Test that analyzed the presence of various bioactive components. The results are reproduced in Table IV.

TABLE IV

Fertilizer Analysis of the SAP Product of Example 2.

| Nutrient | % Available |
|---|---|
| Nitrogen | 5.66 |
| Ammonia | 2.47 |
| Phosphorus | 7.96 |
| $P_2O_5$ | 18.24 |
| Potassium | 3.94 |
| $K_2O$ | 4.74 |
| Calcium | <0.01 |
| Magnesium | <0.01 |
| Sodium | 0.18 |
| Boron | 219.79 |
| Iron | 847.58 |
| Manganese | 673.47 |
| Copper | 452.49 |
| Zinc | 462.74 |
| Monoammonium Phosphate | 20.28 |

EXAMPLE 3

Spray Application of Miracle-Gro™ Pesticide to SAP Particles

SAP particles having a mesh size of between about 10 and about 20 were made according to the method described in Example 1. Between about 6 pints and about 8 pints of Miracle-Gro™ pesticide was sprayed onto about 1 lb. of SAP product using a standard, commercially available garden sprayer. The resulting particles of starch-based SAP product were agitated to ensure that the Miracle-Gro™ pesticide was evenly distributed. Following spraying, the SAP particles were slightly tinted green.

EXAMPLE 4

Inclusion of Miracle-Gro™ Pesticide in the SAP Dough

Distilled water (1,400 ml) was placed in a 3-liter resin kettle and was subjected to constant agitation with a stirrer. Starch flour or meal (110 g) was slowly added to the kettle, and the resulting mixture was stirred for approximately five minutes. A slow stream of nitrogen gas was added to the mixture while the mixture was heated until it reached a temperature of approximately 95° C. The mixture was maintained at this temperature and stirred for approximately 45 minutes to ensure that the starch was gelatinized. The heating mantle was then removed, and the resin kettle was placed in a cold-water bath. The mixture was continuously stirred under nitrogen until the temperature reached 25° C. Acrylonitrile (115 g) and 2-acrylamido-2-methyl-propanesulfonic acid (23 g) were added. The resulting mixture was continuously stirred under nitrogen for approximately 10 minutes. A catalyst solution including cerium ammonium nitrate (5.5 g) dissolved in 0.1M nitric acid solution (50 ml) was added to the mixture while the mixture cooled. The mixture was continuously stirred under nitrogen while the resin kettle remained in the cold-water bath for approximately 60 minutes. The temperature of the mixture at the end of the 60 minutes was approximately 40° C. A solution including potassium hydroxide flakes (90 g) dissolved in water (200 g) was added to the mixture during stirring and heating. The mixture was stirred and heated until a temperature of 95° C. was achieved, after which the mixture was stirred for an additional 60 minutes. The mixture was then neutralized to a pH of 7.5 using a 10% solution of hydrochloric acid. The dough was then cooled to a temperature of about 40° C. Approximately 12 pints of liquid Miracle-Gro™ pesticide was added to about one lb. of dough. The resulting slightly green-tinted dough was agitated for approximately 30 minutes to ensure intimate mixing of the Miracle-Gro™ pesticide and the SAP dough. The resulting dough was extruded into granules. In one implementation, a pasta maker was used to extrude rod-shaped granules. Following extrusion, the granules were dried. Because the rod-shaped granules were sticky, they were dusted with sufficient clay, starch, flour, cellulose, or celite to remove the stickiness. In one implementation, the rod-shaped granules were ground into particles having a desired particle size. Optionally, fine particles could be formed into pellets having a desired size. The process of pelletizing is well known to those skilled in the art.

EXAMPLE 5

Inclusion of Ammonium Phosphate in the SAP Dough

Distilled water (1,400 ml) was placed in a 3-liter resin kettle and was subjected to constant agitation with a stirrer. Starch flour or meal (115 g) was slowly added to the kettle, and the resulting mixture was stirred for approximately five minutes. A slow stream of nitrogen gas was added to the mixture while the mixture was heated until it reached a temperature of approximately 95° C. The mixture was maintained at this temperature and stirred for approximately 45 minutes to ensure that the starch was gelatinized. The heating mantle was then removed, and the resin kettle was placed in a cold-water bath. The mixture was continuously stirred under nitrogen until the temperature reached 25° C. Acrylonitrile (115 g) and 2-acrylamido-2-methyl-propanesulfonic acid (23 g) were added. The resulting mixture was continuously stirred under nitrogen for approximately 10 minutes. A catalyst solution including cerium ammonium nitrate (5.5 g) dissolved in 0.1M nitric acid solution (50 ml) was added to the mixture while the mixture was cooled. The mixture was continuously stirred under nitrogen while the resin kettle remained in the cold-water bath for approximately 60 minutes. The temperature of the mixture at the end of the 60 minutes was approximately 40° C. A solution including potassium hydroxide flakes (90 g) dissolved in water (200 g) was added to the mixture during stirring and heating. The mixture was stirred and heated until a temperature of 95° C. was achieved, after which the mixture was stirred for an additional 60 minutes. The mixture was then neutralized to a pH of 7.5 using a 10% solution of hydrochloric acid. The dough was then cooled to a temperature of about 40° C. Approximately 36.5 g of ammonium phosphate was added directly to about one lb. of dough. The resulting dough was agitated for approximately 30 minutes to ensure intimate mixing of the ammonium phosphate and the SAP dough. The resulting dough was extruded into granules. In one implementation, a pasta maker was used to extrude rod-shaped granules. Following extrusion, the granules were dried. Because the rod-shaped granules were sticky, they were dusted with sufficient clay, starch, flour, cellulose, or celite to remove the stickiness. In one implementation, the rod-shaped granules were ground into particles having a desired particle size. Optionally, fine particles could be formed into pellets having a desired size. The process of pelletizing is well known to those skilled in the art.

Those skilled in the art will recognize that the methods and compositions disclosed herein may be arranged and practiced in a wide variety of different configurations, such as without one or more of the specific details described, or with other methods, compositions, materials, etc. In some cases, well-known materials, compositions or method steps are not described in detail. Furthermore, the described components, method steps, compositions, etc., may be combined in any suitable manner in one or more embodiments. Various modifications, changes, and variations which will be apparent to those skilled in the art may be made in the arrangement, operation, and details of the components, compositions and methods disclosed herein without departing from the spirit and scope of the following claims.

What is claimed is:

1. A method for delivering a beneficial additive in agricultural applications, comprising:
    obtaining at least one beneficial additive combined with a superabsorbent polymer comprising starch graft copolymer particles formed from a process comprising:
        graft polymerizing a monomer onto a starch to form a starch graft copolymer including a starch matrix;
        isolating the starch graft copolymer;
        forming particles of starch graft copolymer that are sized for use in agricultural applications, wherein forming particles comprises extruding the starch graft copolymers into strands and applying an alcohol to the strands to reduce tackiness of the extruded strands, the alcohol chosen from methanol, ethanol, propanol or isopropanol, and forming starch graft copolymer particles sized between 16 and 30 mesh; and
        adding the at least one beneficial additive after isolating the starch graft copolymer so that at least some of the beneficial additive is entrapped by the starch matrix;
    dispensing the combined beneficial additive and superabsorbent polymer in an agricultural environment;
    wherein at least some of the at least one beneficial additive is entrapped by a starch matrix of the starch graft copolymer particles.

2. The method of claim 1, wherein the agricultural environment comprises plant growing media and dispensing the combined beneficial additive and superabsorbent polymer comprises depositing the combined beneficial additive and superabsorbent polymer into the plant growing media adjacent an actual or anticipated location of a plant root system.

3. The method of claim 1, wherein the agricultural environment comprises plant growing media and dispensing the combined beneficial additive and superabsorbent polymer comprises depositing the combined beneficial additive and superabsorbent polymer on a surface of the plant growing media.

4. The method of claim 1, wherein the step of dispensing the combined beneficial additive and superabsorbent polymer occurs previous to planting a plant, seed or seedling.

5. The method of claim 1, wherein the step of dispensing the combined beneficial additive and superabsorbent polymer occurs subsequent to planting a plant, seed or seedling.

6. The method of claim 1, wherein dispensing the combined beneficial additive and superabsorbent polymer in an agricultural environment comprises dispensing the combined beneficial additive and superabsorbent polymer onto a plant structure.

7. The method of claim 1, wherein dispensing the combined beneficial additive and superabsorbent polymer comprises using a spray applicator to dispense the combined beneficial additive and superabsorbent polymer in substantially liquid form.

8. The method of claim 7, wherein a percent concentration by weight of superabsorbent polymer in the combined beneficial additive and superabsorbent polymer mixture is from about 0.5 percent to about 2.0 percent.

9. The method of claim 1, wherein dispensing the combined beneficial additive and superabsorbent polymer comprises using a granular applicator to dispense the combined beneficial additive and superabsorbent polymer in substantially granular form.

10. The method of claim 1, wherein dispensing the combined beneficial additive and superabsorbent polymer is accomplished in conjunction with use of a cultivator.

11. The method of claim 1, wherein the superabsorbent polymer comprises acrylonitrile monomers.

12. The method of claim 1, wherein the superabsorbent polymer comprises monomers that are chosen from: acrylic acid, acrylamide, methacrylamide, 2-acrylamido-2-methyl-propanesulfonic acid, methacrylic acid, vinyl sulfonic acid, ethyl acrylate, potassium acrylate, and derivatives and mixtures thereof.

13. The method of claim 1, wherein the superabsorbent polymer is configured to release the beneficial additive from the starch matrix to the agricultural environment over time.

14. The method of claim 1, wherein the superabsorbent polymer is configured to function as an anti-transpiration agent to the beneficial additive.

15. The method of claim 1, further comprising adhering the combined beneficial additive and superabsorbent polymer to a primary target site of action within the agricultural environment.

16. The method of claim 1, wherein the at least one beneficial additive is chosen from fertilizers, pesticides, plant-growth hormones, plant activators, plant-growth regulators, mycorrhizal fungi, kelp products, soil-based nutrients, derivatives thereof and mixtures thereof.

17. The method of claim 16, wherein the at least one beneficial additive comprises a pesticide chosen from acaricides, algicides, antifeedants, avicides, bactericides, bird repellents, chemosterilants, fungicides, herbicide safeners, herbicides, insect attractants, insect repellents, insecticides, mammal repellents, mating disruptors, microbial pesticides such as bacillus thuringiensis and mycorrhizal fungi, molluscicides, nematicides, rodenticides, synergists, virucides, derivatives thereof and mixtures thereof.

18. A method for delivering a superabsorbent polymer product in agricultural applications, comprising:
    obtaining starch graft copolymer particles comprising a matrix formed from graft polymerizing a monomer onto a starch, the starch graft copolymer particles formed from forcing the starch graft copolymer matrix through a die plate comprising holes disposed therein with a diameter of between about 1/16 inch to 1/4 inch and applying an alcohol to the starch graft copolymer matrix upon exiting the die plate, the alcohol chosen from methanol, ethanol, propanol or isopropanol, to form starch graft copolymer particles sized between about 8 to about 25 mesh and having a density between about 25 pounds per cubic foot and about 35 pounds per cubic foot, the starch graft copolymer particles including a first beneficial additive which is entrapped, at least in part, within the starch graft copolymer matrix, the first beneficial additive being applied to the starch graft copolymer matrix after graft polymerizing the monomer onto the starch; and
    dispensing the combined first beneficial additive and starch graft copolymer particles in an agricultural environment.

19. The method of claim 18, wherein the monomer comprises acrylonitrile monomers.

20. The method of claim 18, wherein the monomer is chosen from: acrylic acid, acrylamide, methacrylamide, 2-acrylamido-2-methyl-propanesuifonic acid, methacrylic acid, vinyl sulfonic acid, ethyl acrylate, potassium acrylate, and derivatives and mixtures thereof.

21. The method of claim 18, wherein the first beneficial additive is entrapped within the starch graft copolymer matrix by mixing the first beneficial additive with a superabsorbent polymer dough during manufacture of the superabsorbent polymer product.

22. The method of claim 18, further comprising a second beneficial additive which is disposed on an exterior of the starch graft copolymer.

23. The method of claim 22, wherein the first and second beneficial additives are substantially the same.

24. The method of claim 18, further comprising a binder coupled to the first beneficial additive, wherein the binder is configured to release the first beneficial additive after a period of time.

25. The method of claim 18, wherein the starch graft copolymer matrix is configured to release the first beneficial additive from the matrix over a period of time.

26. The method of claim 18, wherein the starch graft copolymer matrix functions as an anti-transpiration agent to the beneficial additive.

27. The method of claim 18, wherein the superabsorbent polymer product is in substantially liquid form and a percent concentration by weight of starch graft copolymer matrix in the superabsorbent polymer product is from about 0.5 percent to about 2.0 percent.

28. The method of claim 18, wherein the first beneficial additive is chosen from fertilizers, pesticides, plant-growth hormones, plant activators, plant-growth regulators, mycorrhizal fungi, kelp products, soil-based nutrients, derivatives thereof and mixtures thereof.

29. The method of claim 28, wherein the first beneficial additive comprises a pesticide chosen from acaricides, algicides, antifeedants, avicides, bactericides, bird repellents, chemosterilants, fungicides, herbicide safeners, herbicides, insect attractants, insect repellents, insecticides, mammal repellents, mating disruptors, microbial pesticides such as bacillus thuringiensis and mycorrhizal fungi, molluscicides, nematicides, rodenticides, synergists, virucides, derivatives thereof and mixtures thereof.

30. A method for delivering a beneficial additive in agricultural applications, comprising:
    obtaining at least one beneficial additive entrapped within a superabsorbent polymer comprising a starch graft copolymer particle formed from (1) graft polymerizing a monomer onto a starch to form a starch graft copolymer including a starch matrix; (2) isolating the starch graft copolymer; (3) forming particles of starch graft copolymer that are sized for use in agricultural applications, wherein forming particles comprises extruding the starch graft copolymers and applying an alcohol to the extruded starch graft copolymers, the alcohol chosen from methanol, ethanol, propanol or isopropanol, and forming the starch graft copolymers into granules to form starch graft copolymer particles sized between 8 and 25 mesh; and (4) adding the at least one beneficial additive after isolating the starch graft copolymer so that at least some of the beneficial additive is entrapped by the starch matrix; and
    dispensing the combined superabsorbent polymer/beneficial additive in an agricultural environment;

wherein the step of dispensing the combined superabsorbent polymer/beneficial additive comprises a method chosen from:

(i) dispensing the combined superabsorbent polymer/beneficial additive previous to planting a plant, seed or seedling;

(ii) dispensing the combined superabsorbent polymer/beneficial additive subsequent to planting a plant, seed or seedling;

(iii) dispensing the combined superabsorbent polymer/beneficial additive onto a plant structure;

(iv) dispensing the combined superabsorbent polymer/beneficial additive in substantially liquid form using a spray applicator;

(v) dispensing the combined superabsorbent polymer/beneficial additive using a granular applicator; and (vi) dispensing the combined superabsorbent polymer/beneficial additive using a cultivator.

31. The method of claim 1, wherein dispensing the combined beneficial additive and superabsorbent polymer in an agricultural environment comprises applying between one and eight pounds of starch graft copolymer per acre.

* * * * *